(12) United States Patent
Pendekanti et al.

(10) Patent No.: US 7,179,254 B2
(45) Date of Patent: Feb. 20, 2007

(54) HIGH INTENSITY ABLATION DEVICE

(75) Inventors: Rajesh Pendekanti, Bridgewater, NJ (US); Vaclav O. Podany, New Fairfield, CT (US)

(73) Assignee: Ethicon, Inc., Somerville, NJ (US)

( * ) Notice: Subject to any disclaimer, the term of this patent is extended or adjusted under 35 U.S.C. 154(b) by 202 days.

(21) Appl. No.: 10/799,242

(22) Filed: Mar. 9, 2004

(65) Prior Publication Data

US 2005/0203499 A1    Sep. 15, 2005

(51) Int. Cl.
*A61B 18/18*    (2006.01)
(52) U.S. Cl. ............... 606/28; 606/51; 606/207
(58) Field of Classification Search ......... 606/27–31, 606/41, 45–52, 206, 207, 169
See application file for complete search history.

(56) References Cited

U.S. PATENT DOCUMENTS

| | | | |
|---|---|---|---|
| 4,074,718 A * | 2/1978 | Morrison, Jr. ............... | 606/45 |
| 4,240,431 A * | 12/1980 | Komiya ..................... | 606/15 |
| 4,872,456 A | 10/1989 | Hasson | |
| 5,322,055 A * | 6/1994 | Davison et al. ............... | 601/2 |
| 5,626,607 A * | 5/1997 | Malecki et al. ............. | 606/205 |
| 6,267,760 B1 | 7/2001 | Swanson | |
| 6,447,433 B1 | 9/2002 | Reyes | |
| 6,517,536 B2 | 2/2003 | Hooven et al. | |
| 6,527,767 B2 | 3/2003 | Wang et al. | |
| 6,546,935 B2 | 4/2003 | Hooven | |
| 6,558,382 B2 | 5/2003 | Jahns et al. | |
| 6,723,092 B2 * | 4/2004 | Brown et al. ............... | 606/41 |
| 6,775,575 B2 * | 8/2004 | Bommannan et al. ......... | 607/101 |
| 6,821,273 B2 * | 11/2004 | Mollenauer ................. | 606/28 |
| 6,953,461 B2 * | 10/2005 | McClurken et al. ......... | 606/51 |
| 2002/0120263 A1 | 8/2002 | Brown et al. | |
| 2002/0128639 A1 | 9/2002 | Pless et al. | |
| 2003/0028187 A1 | 2/2003 | Vaska et al. | |
| 2003/0032952 A1 | 2/2003 | Hooven | |
| 2003/0216733 A1 | 11/2003 | McClurken et al. | |
| 2004/0111101 A1 | 6/2004 | Chin | |

* cited by examiner

*Primary Examiner*—Michael Peffley (57) ABSTRACT

An apparatus for ablating tissue, the apparatus having first and second opposing jaws operative to compress tissue to be allayed therebetween, the first jaw having a first ablation surface directing ablative energy into the tissue and the second jaw having a second ablation surface reflecting incident ablative energy into the tissue. The ablative energy may be ultrasonic, microwave, cryoablation, radio-frequency, photodynamic, laser, and cautery energy. The instrument may also have a pointed tip for piercing tissue, allowing the instrument to clamp the tissue wall of a hollow organ before ablation. Alternately, the instrument may clamp two or more tissue layers of a hollow organ without piercing prior to clamping an ablation.

14 Claims, 8 Drawing Sheets

HIGH INTENSITY ABLATION DEVICE

BACKGROUND OF THE INVENTION

1. Field of Invention

The present invention relates generally to surgical instruments, and more particularly, to a high intensity ablation device to create linear lesions in tissue, such as a surface of the heart.

2. Description of Related Art

Atrial fibrillation (AF) is a commonly occurring disorder that causes the atria to beat erratically. This condition can cause thromobogenesis and strokes. It can be treated pharmacologically, but many patients are not responsive to these therapies. It is generally accepted that creating lesions in the atria that create conduction blocks are a good way to do this.

There have been a number of procedures developed to treat atrial fibrillation. These include the surgical MAZE procedure, where the heart of the patient is stopped and the left and right atria are opened. The atrium is then divided into pieces and sewn back together. It is presumed that the scars that form from these cuts effectively block electrical conduction in the atria. This technique suffers from all of the morbidities associated with placing the patient on cardiopulmonary bypass and stopping the heart. Further, it is a time consuming and technically difficult procedure to perform.

There are also a number of catheter based interventional techniques that use RF energy or cooling to ablate the tissue and form scarring. These require mapping of the aberrant foci within the atria, and then the selective ablation of the foci. This too is a time consuming and difficult procedure. Ablation catheters are commercially available for this procedure. More recent work suggests that a large majority of patients (perhaps as high as 80%) will have their atrial fibrillation eliminated by ablating circumferentially around the pulmonary veins. A catheter is commercially available that can be inserted percutaneously into the pulmonary veins and used to ablate the tissue in the veins. The drawback to this technique is that ablating circumferentially within the veins may cause pulmonary vein stenosis. It also seems likely that a more complicated lesion set is required to be effective in the majority of patients. It is desirable to have tools and techniques that will allow these lesions to be easily created on the myocardial tissue rather than the venous wall.

BRIEF SUMMARY OF THE INVENTION

Therefore, it is an object of the present invention to provide a surgical instrument that overcomes the disadvantages associated with retractors of the prior art.

Since the myocardial tissue is about 3–6 mm thick and is significantly thicker than the venous wall, the lesions need to be transmural in order for the lesion to be effective in creating a line of electrical block to treat AF. Typical existing instruments may not be able to guarantee a transmural lesion and/or may compromise tissue structure and/or form coagulum/thrombus. The present invention discloses a system to overcome the limitations of the prior art by providing an instrument whose performance is enhanced by clamping. The present invention further overcomes the limitations of the prior art by allowing the conduction blocks to be created from either the epicardial or the endocardial surface or both, and can be performed on a beating heart or an externally perfused heart.

Disclosed is an apparatus for ablating tissue, the apparatus having first and second opposing jaws operative to compress tissue to be ablated therebetween, the first jaw having a first ablation surface directing ablative energy into the tissue and the second jaw having a second ablation surface reflecting incident ablative energy into the tissue. The ablative energy may be one of ultrasonic, microwave, cryoablation, radio-frequency, and laser energy. The instrument may also have a pointed tip for piercing tissue, allowing the instrument to clamp the tissue wall of a hollow organ before ablation. Alternately, the instrument may clamp two or more tissue layers of a hollow organ without piercing prior to clamping and ablation.

BRIEF DESCRIPTION OF THE DRAWINGS

These and other features, aspects, and advantages of the present invention will become better understood with reference to the following description, appended claims, and accompanying drawings, with like reference numerals referring to like features across the several views, where:

DETAILED DESCRIPTION OF THE INVENTION

Although this invention is applicable to numerous and various types of surgical instruments for ablation of tissue, it has been found particularly useful in the environment of a surgical instrument that utilizes ultrasound energy to ablate/coagulate/cauterize and/or create lesions in tissue (collectively referred to herein as ablation). Other forms of ablative energy include, but are not limited to, microwave, cryoablation, radio-frequency (RF), and laser energy. Therefore, without limiting the applicability of the invention to ultrasound energy, the invention will be described in such environment. Those skilled in the art will appreciate that other forms of energy may be utilized in the instrument of the present invention to ablate tissue.

Figure 1:
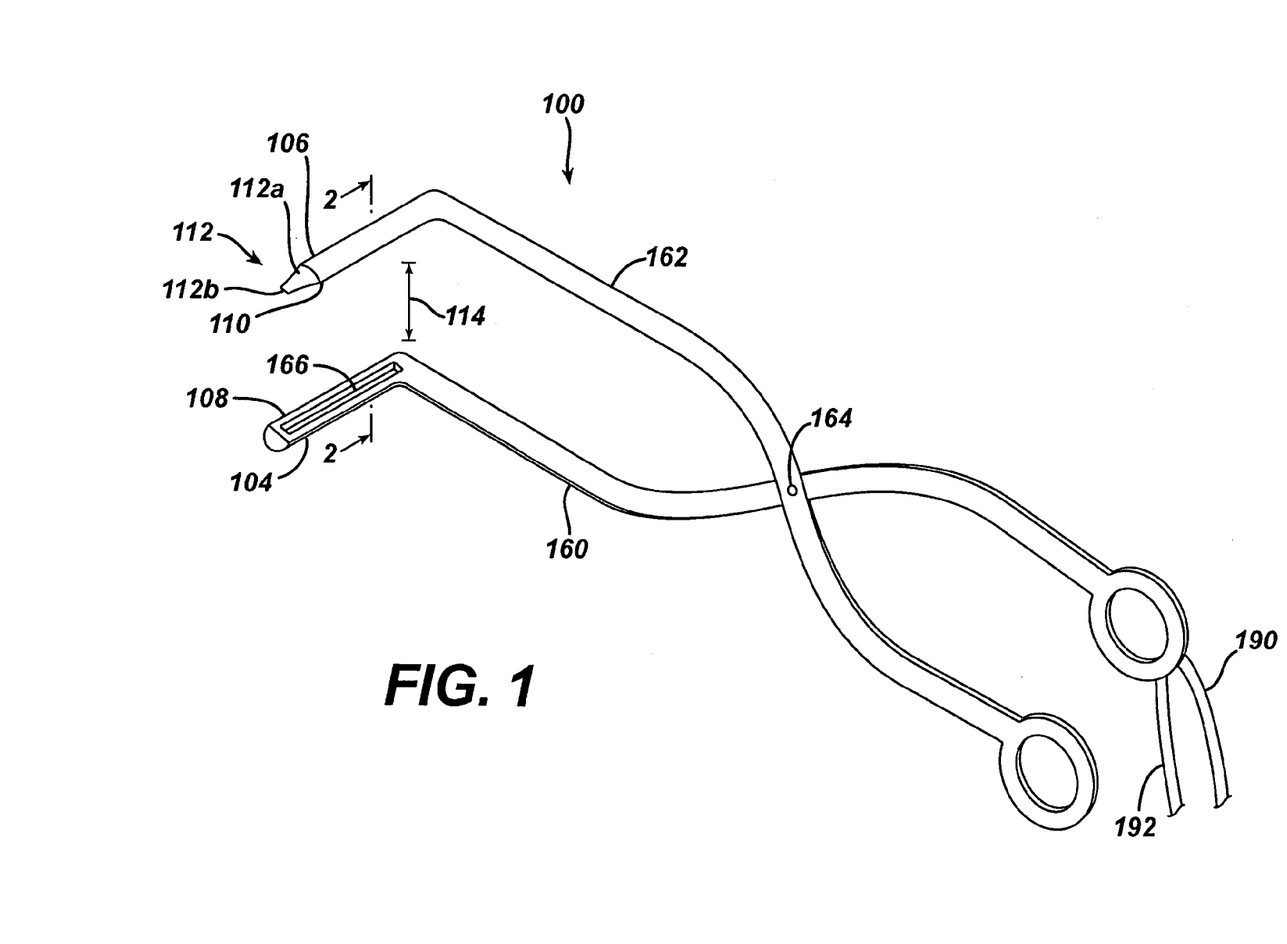
FIG. 1 illustrates an isometric view of a first embodiment of the surgical instrument of the present invention.

Referring now to FIG. 1, there is shown a preferred implementation of a surgical instrument of the present invention, the instrument being generally referred to by reference numeral 100. The instrument 100 is shown configured for open surgical procedures by way of example only. Those skilled in the art will appreciate that the instrument 100 can also be used in less invasive and minimally invasive procedures. If configured for minimally invasive procedures, the instrument is shaped and sized such that its distal end can pass through incisions or ports in the body, such as through a trocar tube, as is known in the endoscopic arts. The instrument 100 may also be configured and constructed of materials for either a disposable or reusable version and for proper cleaning and sterilization, if necessary. Configuration of surgical instruments to be reusable, disposable, as well as to be cleaned and/or sterilized are well known in the medical instrumentation arts.

Referring now to FIG. 1, in a first embodiment the instrument, generally 100, generally has a distal end 102 having first elongated jaw 104 and second elongated jaw 106. Each of the first and second elongated jaws 104, 106 has a respective first ablation surface 108 and second ablation surface 110. As will be described in more detail, an ablation surface can comprise a surface adjacent or part of a source of ablative energy, or a surface reflecting incident ablative energy. At least one of the first and second elongated jaws 104, 106 may include a pointed distal tip 112 useful for piercing tissue. Preferably, the pointed distal tip 112 comprises a tapered surface 112a terminating in a sharp leading edge 112b. Those skilled in the art will appreciate that the pointed distal tip 112 may be configured in many ways without departing from the scope or spirit of the present invention. For example, the pointed distal tip 112 may be conical and terminate in a point or have two tapered surfaces, each of which terminate in a common sharp leading edge. Whatever the configuration of the pointed distal tip 112, its purpose is to pierce tissue such that the corresponding first or second elongated jaw 104, 106 can be properly positioned to cooperatively ablate a selected tissue with the respective second of first elongated jaw 106, 104.

The first and second elongated jaws 104, 106 are carried on the distal ends of first arm 160 and second arm 162, respectively. First and second arms 160, 162 are joined at fulcrum 164, for example a pin, in a manner to allow the arms 160, 162 to pivot relative to each other. In the embodiment shown, first and second elongated jaws 104, 106 are formed at right angles to the first and second arms 160, 162. This has the advantage of opening and closing the first and second elongated jaws 104, 106 in a parallel fashion to one another as the arms 160, 162 are pivoted. This parallel alignment is desirable when one of ablation surfaces 108, 110 are an active source of ablative energy, and the other is a reflector of incident ablative energy. However, in alternate embodiments, the elongated jaws 104, 106 may be formed at another angle to, or aligned with, arms 160, 162.

Figure 3:
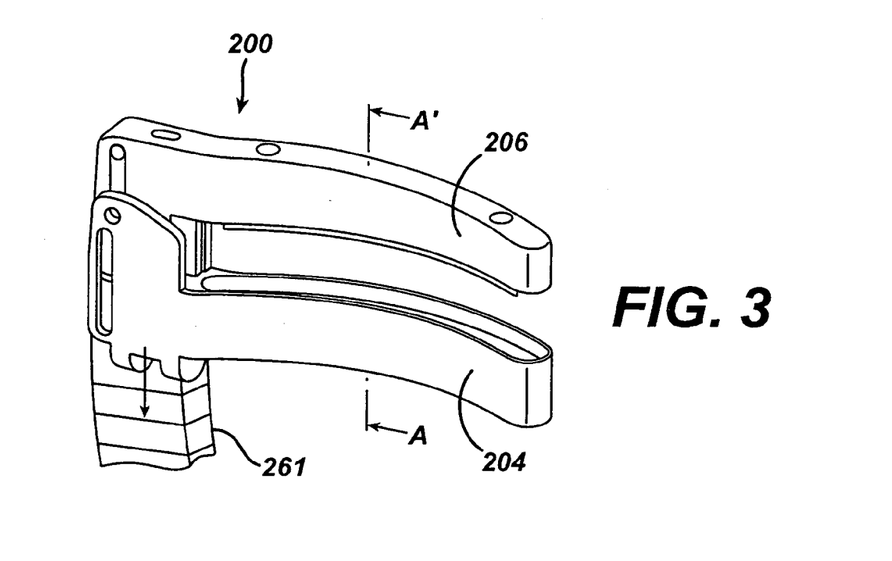
FIG. 3 illustrates an isometric view of a second embodiment of the surgical instrument of the present invention.

The first and second elongated jaws 104, 106 are movable between open and closed positions. The first and second ablation surfaces 108, 110 oppose each other, at least where the first and second elongated jaws 104, 106 are in the closed position. Although, the first and second ablation surfaces 108, 110 may come into contact when the first and second jaws 104, 106 are in the closed position, it is preferred that a gap 114 remain between the same to prevent overclamping and trauma to the tissue. Additionally, the gap 114 can prevent accidental shorting where the first and second ablation surfaces 108, 110 are energized with RF energy. Alternatively, the instrument 100 can include means for varying the size of the gap 114 from zero to a preferred gap for the particular procedure being performed. The first and second elongated jaws are preferably long and narrow, preferably having a length in the range of about 3 cm to about 8 cm, and more preferably about 5 cm. First and second elongated jaws 104, 106 and can be linear, as shown, or curved, as illustrated in FIG. 3, or may have a combination of both linear and curved portions.

The instrument comprises ablation means, for example an ultrasonic transducer 166 for supplying ultrasonic energy to at least one of the first and second ablation surfaces 108, 110. Ultrasonic energy is delivered to the ablation surfaces 108, 110 of the first and second jaws 104, 106 and may be focused into the tissue being ablated. An ultrasonic generator, as is known in the art, is used to generate ultrasonic energy for delivery to the ablation surfaces 108, 110 of the first and second jaws 104, 106 via either or both of arms 160, 162. The ultrasonic generator can be integral with the instrument 100 or separate therefrom.

In the embodiment of FIG. 1, ultrasonic energy, or alternately power for driving the ultrasonic generator are supplied via 190. Cooling fluid, for example degassed saline, is supplied via 192. Cooling fluid may be circulated through the instrument and out the proximal end, or may be flushed out at or near the distal end 102. Provision for both open and closed coolant circulation may be made to provide the surgeon with irrigation option in the instrument.

Figure 2:
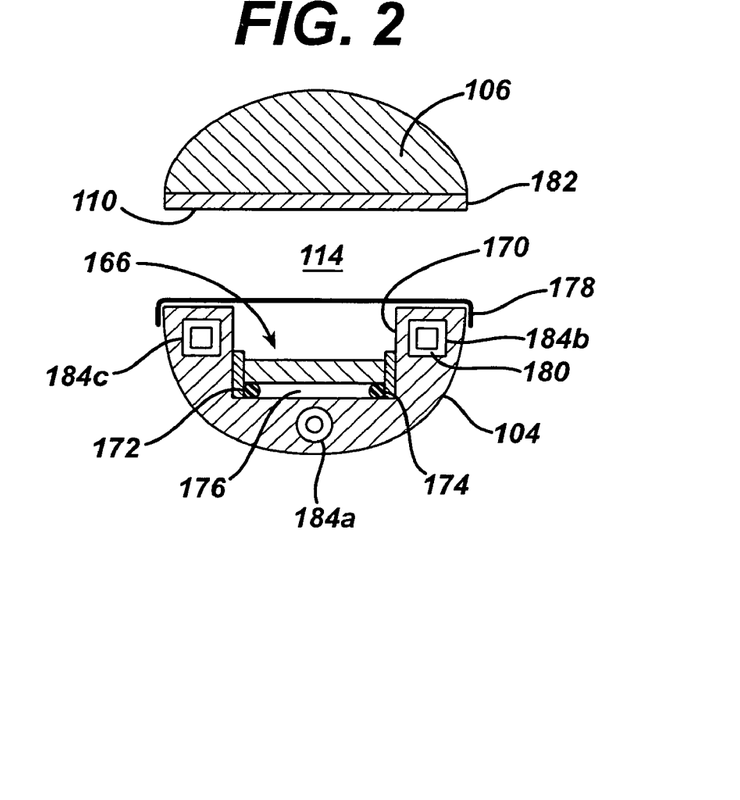
FIG. 2 illustrates a cross-sectional view of the elongated jaws of the instrument of FIG. 1, taken along section line 2—2, with first and second elongated jaws in an open position.

Turning now to FIG. 2, shown is a cross-sectional view of the first and second elongated jaws 104, 106 in an open position. Exemplary embodiments of ablative transducers are disclosed in detail in U.S. patent application Ser. No. 10/675,891, filed 30 Sep., 2003, the complete disclosure of which is hereby incorporated by reference in its entirety for all purposes. Any of the features disclosed therein as enhancing ablation efficacy may be employed in the present invention, however, certain among these will be described further.

Ultrasonic transducer 166 is provided in first elongated jaw 104. Transducer element 168, for example a piezoelectric crystal, may be secured in a cavity 170, for example by a sealant 172. Spacer 174 may be provided to create an air backing chamber 176, which can enhance the acoustic efficiency of the transducer element 168. The cavity 170 is closed by a membrane 178 which may be a compliant and acoustically transparent material, for example PEEK, PET, polystyrene, ULTEM, or the like. The space between membrane 178 and element 168 may form a passage 180 for coolant. Coolant fluid also serves to match acoustic impedance and provide ultrasonic coupling between the transducer element 168 and the membrane 178 or first ablation surface 108.

The opposing second elongated jaw 106 may be provided on its second ablative surface 110 with an acoustic reflector 182. Any material with an acoustic impedance significantly higher or lower than the tissue being ablated may be used as an acoustic reflector. Example materials include air-filled foam such as expanded GORE-TEX, polystyrene, or a stainless steel.

In addition to the embodiment as illustrated, an acoustic reflector 182 may be located on the first elongated jaw 104 in addition to or in place of that on the second elongated jaw 106. Further, an ultrasonic transducer 166 may be located on the second elongated jaw 106 in addition to or in place of that on the first elongated jaw 104.

Alternately or additionally, the instrument 100 may be provided with a heat exchangers 184*a*, 184*b*, 184*c*, to carry excess heat generated by the instrument away from the distal end 102. Fewer or greater numbers of heat exchangers may be provided without departing from the scope of the invention. In one embodiment, the heat exchangers 184*a*, 184*b*, 184*c* are heat pipes. Alternately or additionally, heat exchanges can be in the form of: a heat sink with fins for radiation and convection; a fluid exchangers, including cooled fluids, liquid or gas, for example as described supra; solid state cooling elements, for example Peltier effect cooling elements.

Figure 2A:
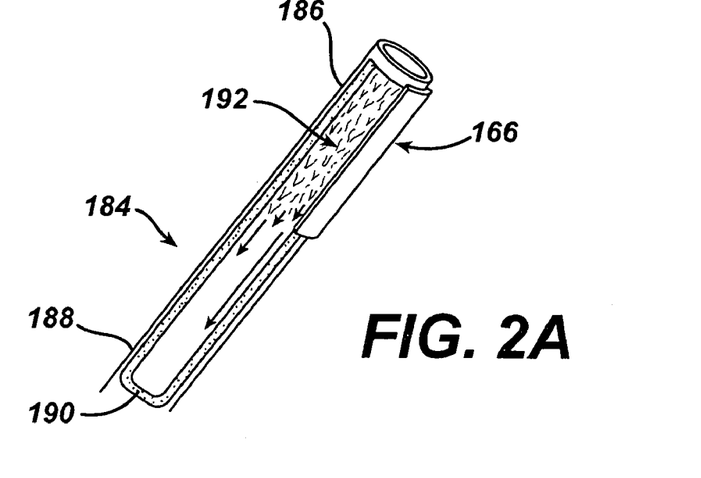
FIG. 2(A) illustrates the operation of a heat pipe as applied to the present invention.

Referring now to FIG. 2A, the operation of the heat pipe will be described. Illustrated simply are a heat pipe 184 and an ultrasonic transducer 166. Heat pipes are generally known in the art, and examples are sold by Acrolab, Ltd. of Windsor, Ontario, Canada under the ISOBARS brand name. The heat pipe 184 consists of an evaporator end 186 and a condenser end 188. Within the interior of the heat pipe 184, typically adhered to an inner surface, is an absorbent material 190. A working fluid 192 is introduced into the interior of the heat pipe, preferably up to the saturation point of the absorbent material 190. The interior of the heat pipe 184 is advantageously under vacuum. The evaporator end 186 would be positioned adjacent the ultrasonic transducer 166 and/or the surface of the tissue to be ablated. As energy is applied to the ultrasonic transducer 166, for example during ablation, heat is generated at the evaporator end 186, the evaporator end 186 heats up. This causes a phase change in the working fluid 192. The phase change creates a pressure gradient, which forces the vapor along the length of the heat pipe 184 to the condenser end 188. The vapor carries heat away from the evaporator end 186 with it, thereby regulating temperature. At the condenser end 188, the working fluid 192 releases its carried heat to the ambient surroundings, and condenses, reentering the absorbent material 190. Gravity and/or capillary action draws the working fluid 192 back to the evaporator end 186.

As implemented in FIG. 2, heat exchangers 184*b* and 184*c* act to regulate temperature both in the transducer 166, as well as at the ablation-tissue interface. Thermal spikes that lead to popping are thereby prevented. Tissue popping is known to be associated with adverse effects, including intramural steam formation and subsequent avulsion, cleaving, or blood loss. Heat exchangers such as heat pipe 184 reduce the need for other indirect temperature control techniques, including pulsing RF power and temperature feedback. Energy delivery feedback control is time consuming by comparison and may substantially increase the ablation cycle time.

It should be noted that this reflective concept is equally applicable to ablative energy sources which are not, strictly speaking, reflective, as is the case of ultrasonic, microwave, or laser energy. For example, in a cryoablation embodiment, providing a thermally reflective surface, one that provides a thermal barrier, on a jaw surface limits the heat transfer beyond the reflector. Heat flow into the tissue through the jaw is reduced, thus minimizing the heat losses and enhancing the ablative effect. Similarly if direct application of heat is the source of ablative energy, the effect of thermally isolating the tissue will be beneficial. Therefore, a reflective surface should be read to include not only a surface which incurs and redirects incident energy, but a surface that alters a flow of a particular form of energy by its presence in that energy's path, as in the case of an insulating surface as described.

Figure 13:
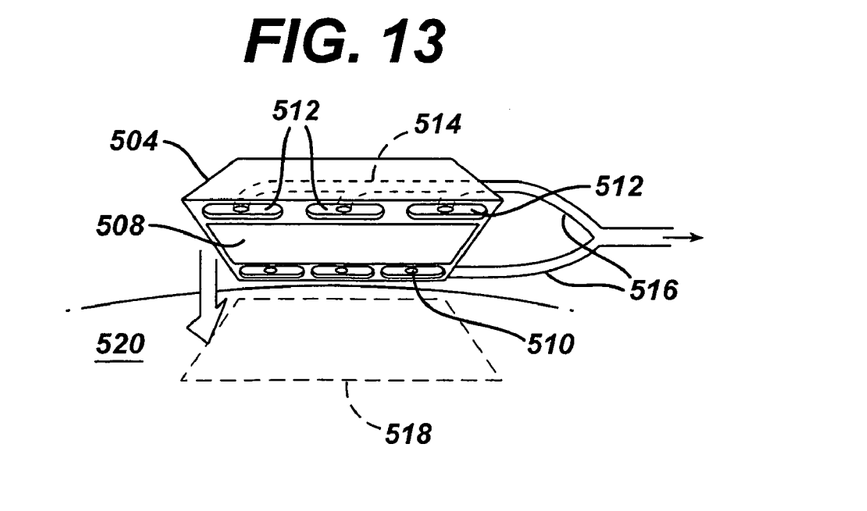
FIG. 13 illustrates an additional feature of the surgical instrument of the present invention, which may be incorporated into any of the above embodiments.

Referring now to FIG. 13, an additional feature is illustrated which may be incorporated into this or other embodiments irrespective of the features already described. Other features described herein have been omitted from FIG. 13 for clarity. Shown is an ablation transducer 504, for example one of two jaws as described, supra. The ablation transducer 504 includes a first ablation surface 508. One or more suction ports 510 are positioned at the periphery of the ablation surface 508. Preferably, several suction ports 510 are aligned along opposite sides of the length of the ablation surface 508. More preferably, suction ports 510 are provided in recesses 512. Suction ports 510 are in communication with a source of negative pressure, for example through internal passages 514, and/or external lines 516.

Outline 518 defines the footprint of the ablation transducer on the surface of the tissue 520. Where the tissue is muscle, for example the heart, the tissue is prone to spontaneous contraction and/or movement. Movement between the tissue and the transducer can cause undesirable peripheral tissue damage and/or hinder the intended ablation. Therefore, prevention of relative movement between the tissue and the transducer is desirable. As described elsewhere, according to one aspect of the present invention, applying a clamping force to the tissue can accomplish that objective, in addition to other benefits. Alternately or additionally, applying suction to the ports adjacent the ablative surface can also immobilize the tissue relative to the transducer.

The suction immobilization is useful in the opposing jaw embodiment described, or without an opposing jaw. Optionally, in the jaw embodiment, suction immobilization may be located on the second jaw in place of or in addition to the first jaw.

Figure 4:
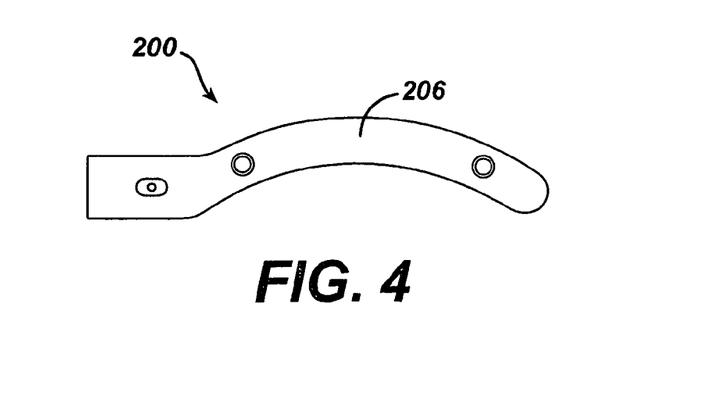
FIG. 4 illustrates an overhead view of a second embodiment of the surgical instrument of the present invention.
Figure 5:
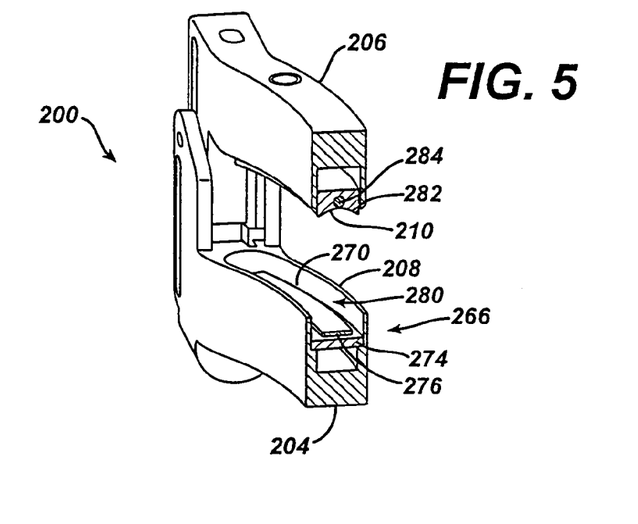
FIG. 5 illustrates a cross-sectional view of a second embodiment of the surgical instrument of the present invention taken through plane A–A' of FIG. 3.

A second embodiment of an ablative clamp, generally 200, is shown in FIGS. 3–5. Clamp 200 has a first elongated jaw 204 and a second elongated jaw 206. As seen in each of FIGS. 3–5, the first and second elongated jaws 204, 206 are curved along their length. The first and second elongated jaws 204, 206 are mounted on the distal end of a shaft 261. In this embodiment, the shaft represent a flexible malleable shaft, a preferred embodiment of which is disclosed in U.S. patent application Ser. No. 10/736,199, filed 15 Dec. 2003, the complete disclosure of which is hereby incorporated by reference. Shaft 261 may also be a rigid shaft, steerable/flexible shaft, or other suitable configuration as is known in the art. In this embodiment, the first and second elongated jaws are articulated to be parallel to each other, for example by an actuating cable or shaft in, on or near shaft 261.

Referring now to FIG. 5, the ablative clamp 200 is shown in cross-section. First elongated jaw 204 has an ultrasonic transducer 266. Transducer element 268 is secured in cavity 270. Spacers 274 form a flexible seal along the length of the transducer element 268 to create an air backing chamber 276. Cavity 270 is closed by a membrane (not shown) which forms the first ablative surface 208. A passage 280 is formed for coolant to flow over the transducer element 268.

Second elongated jaw 206 is provided with a second ablative surface 210, formed by an acoustic reflector 282. In this case, the acoustic reflector is curved to focus the reflected ablative energy upon return to the tissue. Alternately or additionally, the reflector may include a plurality of flat surfaces forming an angle to one another to focus the reflected energy. Also provided are one or more temperature sensors 284. The temperature sensors 284 allow monitoring of the formation of lesions in the tissue throughout the ablative process.

It is also contemplated in this or other embodiments that the ultrasonic transducer 266 be curved or focused in its orientation towards the tissue, for example by employing a curved crystal as described supra, or altering either or both of the angle and the distance between two crystals. The latter aspect is explained further in U.S. patent application Ser. No. 10/609,693 entitled Ultrasonic Radial Focused Transducer for Pulmonary Vein Ablation, filed 30 Jun. 2003, the complete disclosure of which is incorporated by reference for all purposes. The reflector could be either flat or itself focused in such embodiments.

Figure 5A:
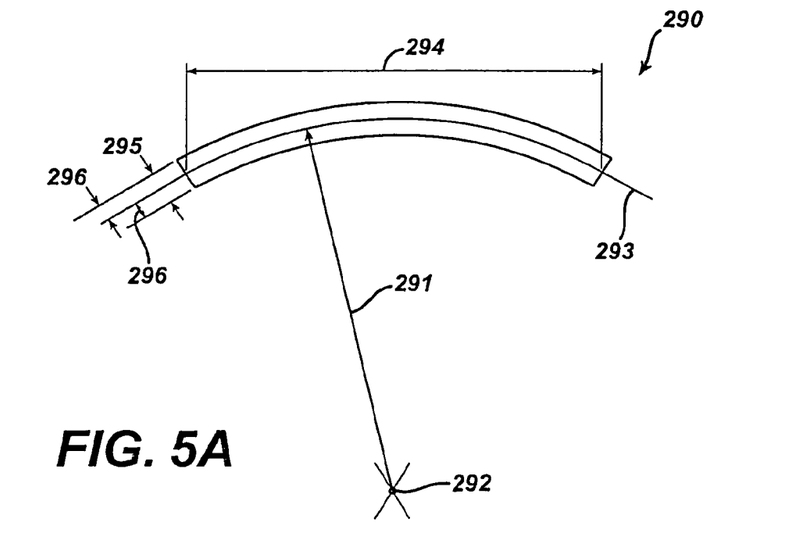
FIG. 5(A) illustrates a plan view of an ultrasonic transducer crystal according to the embodiment of FIGS. 3–5.

Referring now to FIG. 5(A), illustrated in plan view is an ultrasonic transducer crystal 290 according to the embodiment of FIGS. 3–5, though not to scale. In the preferred embodiment, ultrasonic transducer crystal 290 is laterally curved. The curvature is defined by a radius 291, in this case about 2 inches, which converges on a point 292. Curvature is defined along a longitudinal axis 293 of the ultrasonic transducer crystal 290. Preferably, the ultrasonic transducer crystal 290 has a length 294 of about 2 inches, as measured at the longitudinal axis 293. In this embodiment, the ultrasonic transducer crystal 290 has a width 295 of about 0.138 inches. The width 295 is evenly distributed on each side of the longitudinal axis 293 as two approximately equal half-widths 296. The thickness of the ultrasonic transducer crystal 290 is preferably about 0.012 inches.

The ultrasonic transducer crystal 290 is preferably comprised of a PZT-8 grade material, i.e., DOD STD-1376A (SH) Type III ("Navy Type III"), one source of which is the Morgan Electro Ceramics company, another source being the Keramos company as K-278, or their equivalents. However, PZT-4 grade material, i.e., DOD STD-1376A (SH) Type I ("Navy Type I"), its equivalent Keramos K270, or PZT-4D grade material, e.g., K300 by Keramos are acceptable as well. In operation, the ultrasonic transducer crystal 290 is typically driven at a frequency of between about 6.5 MHz and about 9.5 MHz, preferably between about 7.5 MHz and about 8.5 MHz, and more preferably at about 8 MHz. It will be appreciated, however, that variance of the driving frequency may occur as acceptable error, or may be purposefully induced for therapeutic reasons, as described for example in co-pending U.S. patent application Ser. No. 10/675,891, filed 30 Sep. 2003, the complete disclosure of which is hereby incorporated by reference for all purposes.

Figure 6:
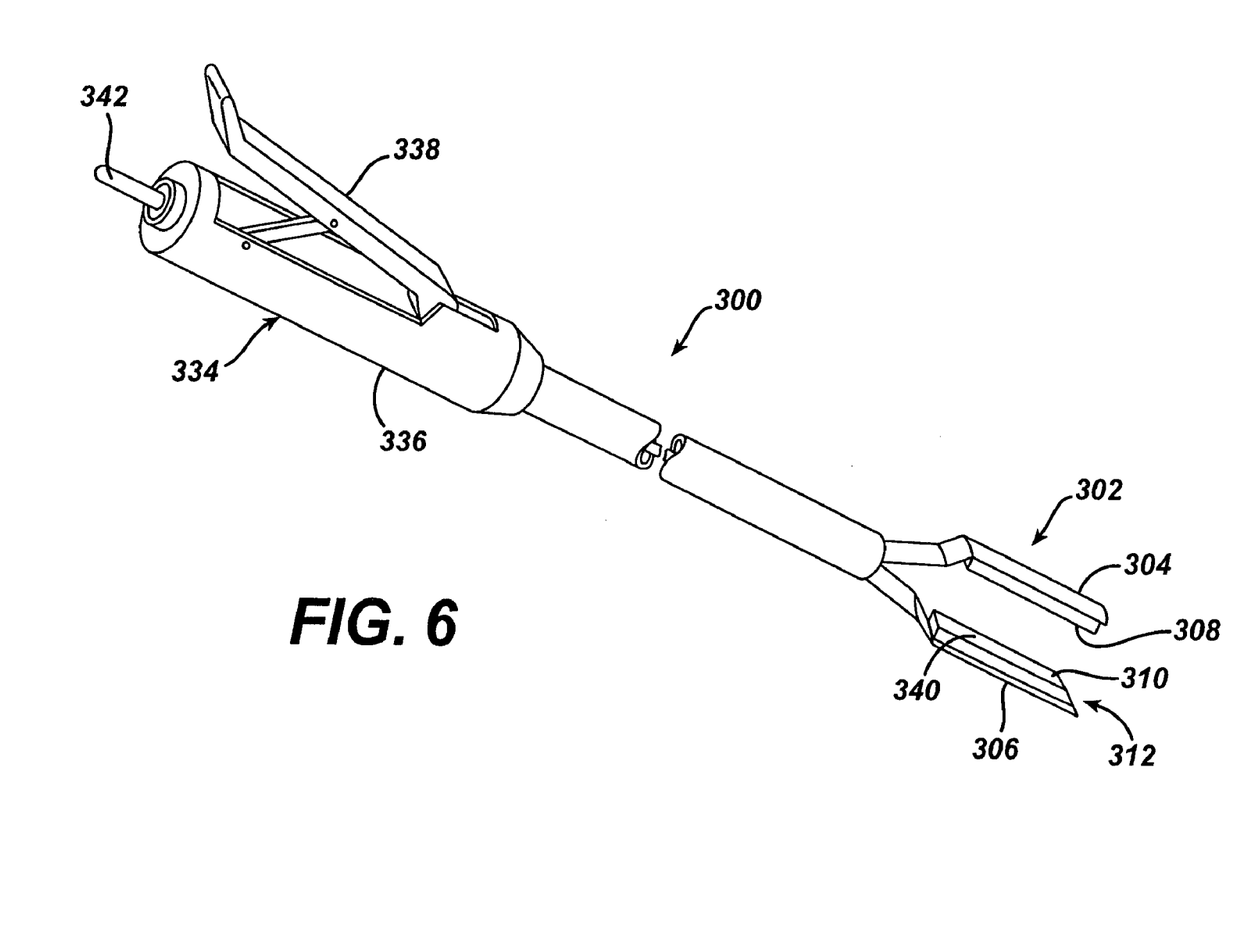
FIG. 6 illustrates an isometric view of a third embodiment of the surgical instrument of the present invention.
Figure 7:
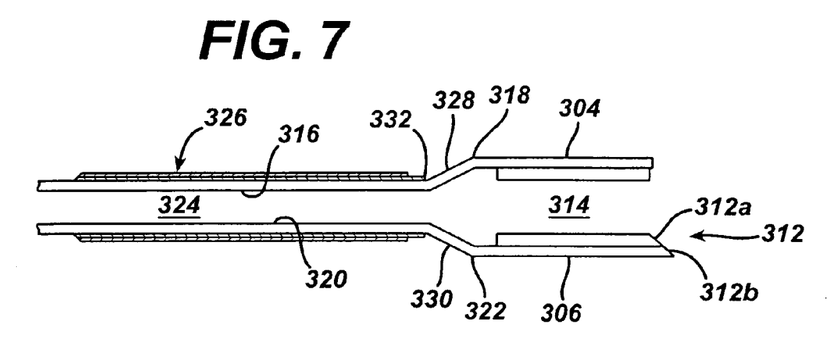
FIG. 7 illustrates a cross-sectional view of the elongated jaws of the instrument of FIG. 6, taken along a longitudinal axis of the instrument, with elongated jaws in an open position.
Figure 8:
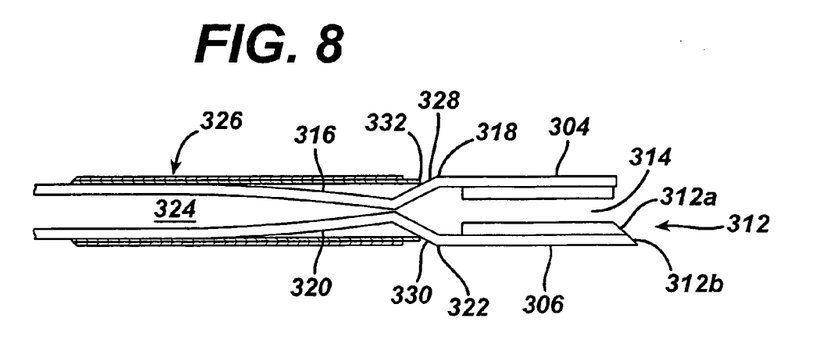
FIG. 8 illustrates the partial sectional view of FIG. 7, with the elongated jaws in a closed position.

Referring now to FIGS. 6–8, in yet another embodiment, the instrument 300 generally has a distal end 302 having first and second elongated jaws 304, 306. Each of the first and second elongated jaws 304, 306 has a corresponding ablation surface 308, 310. At least one of the first and second elongated jaws 304, 306 further has a pointed distal tip 312 useful for piercing tissue. Preferably, the pointed distal tip 312 comprises a tapered surface 312a terminating in a sharp leading edge 312b. Those skilled in the art will appreciate that the pointed distal tip 312 may be configured in many ways without departing from the scope or spirit of the present invention, for example as described above.

The first and second elongated jaws 304, 306 are movable between open and closed positions, as shown in FIGS. 7 and 8, respectively. The first and second ablation surfaces 308, 310 oppose each other, at least where the first and second elongated jaws 304, 306 are in the closed position shown in FIG. 8. Although, the first and second ablation surfaces 308, 310 may come into contact when the first and second jaws 304, 306 are in the closed position, it is preferred that a gap 314 remain between the same to prevent overclamping and trauma to the tissue and to prevent accidental shorting where the first and second ablation surfaces 308, 310 are energized with RF energy. Preferably, the instrument 300 can include means for varying the size of the gap 314 from zero to a preferred gap 314 for the particular procedure being performed, for example as illustrated in FIG. 6, and described further, infra.

The first and second elongated jaws 304, 306 are preferably long and narrow, preferably in the range of 3 cm to about 8 cm, and more preferably about 5 cm. They can be linear, as shown, or curved or have both straight and curved portions.

The instrument 300 further has actuation means for actuating at least one of the first and second elongated jaws 304, 306 between the open and closed positions. Preferably, each of the first and second elongated jaws 304, 306 is movable and actuated between the open and closed positions. However, those skilled in the art will appreciate that one of the first and second elongated jaws 304, 306 may be fixed and the other may be movable between and open and closed position relative to the fixed jaw. As discussed previously, it is beneficial, when ablating the atria, for the first and second elongated jaws 304, 306 to exert a degree of clamping force on the tissue being ablated. Therefore, it is preferred that the actuation means be capable of closing the first and second elongated jaws 304, 306 with a degree of force to apply the proper clamping compression to the tissue. Further, it is preferred that the actuation means have further means for maintaining the first and second elongated jaws 304, 306 in a substantially parallel relationship between the open and closed positions, or at least just before and during the clamping of the tissue between the first and second elongated jaws 304, 306.

Many mechanisms are known in the art for maintaining members in a parallel relationship. Among these mechanisms are linkages that constrain the members to move parallel to each other, such linkages are well known in the art. Still other mechanisms maintain the members in a substantial parallel movement. The latter mechanisms, although they do not truly maintain the members in a parallel movement, they provide a substantially parallel relationship and are often less expensive and complicated than linkage mechanisms and further are smaller in size, which is an important consideration in surgical instrumentation, particularly for endoscopic and minimally invasive surgical instruments. An example of one of the latter mechanisms for maintaining the first and second elongated jaws 304, 306 in a parallel relationship is shown in FIGS. 6–8, and explained in detail in U.S. Pat. No. 5,626,607, the entire contents of which is incorporated herein by its reference.

In general, the preferable means for maintaining the first and second elongated jaws 304, 306 in a parallel relationship has a first elongated rod 316 disposed at a proximal end 318 of the first elongated jaw 304 and a second elongated rod 320 disposed at a proximal end 322 of the second elongated jaw 306. The first and second elongated rods 316, 320 are disposed in a lumen 324 of an elongated tube 326. Preferably, the first and second elongated jaws 304, 306 are biased in the open position by a biasing means. The biasing means preferably comprises a distal end 328, 330 of the first and second elongated rods 316, 318, respectively, being tapered outwards such that they ride or engage on a distal edge 332 of the elongated tube 326. The distal ends 328, 330 and the resiliency of the elongated rods 316, 320 act to bias the first and second elongated jaws 304, 306 in the open position. At least one of the first and second elongated rods 316, 320 or the elongated tube 326 is operatively connected to the actuation means such that actuation thereof forces the first and second elongated jaws 304, 306 into the closed position against a biasing force of the biasing means. In other words, if the elongated tube 326 is pushed distally or one or more of the elongated rods 316, 320 are pulled proximally, the distal ends 328, 330 ride on the distal edge 332 of the elongated tube 326 and force the first and second elongated jaws 304, 306 into the closed position. An opposite actuation allows the first and second elongated jaws 304, 306 to open due to the biasing means. Those skilled in the art will appreciate that the preferred mechanism described above, while not maintaining the first and second elongated jaws 304, 306 in a truly parallel relationship, maintains the first and second elongated jaws 304, 306 in a substantially parallel relationship and has the advantages of being small, uncomplicated, and inexpensive to manufacture.

The actuation means is also preferably configured as disclosed in U.S. Pat. No. 5,626,607 and comprises a handle 334 having a fixed cylindrical body 336 and a movable lever 338 rotatably disposed in the body 336. One of the elongated tube 326 or first and second elongated rods 316, 320 have a proximal end operatively connected to the handle 334. Preferably, the elongated tube 326 is fixed to the handle 334 by means of adhesive, press fit or other means known in the art and one or both of the elongated rods 316, 320 are operatively connected to the lever 338 by way of a linkage or rack and pinion or other means known in the art, such that rotation of the movable lever 338 relative to the fixed cylindrical body 336 actuates the first and second elongated jaws 304, 306 into the closed position as discussed above, and an opposite rotation of the movable lever 338 relative to the fixed cylindrical body 336 actuates the first and second elongated jaws 304, 306 into the open position, as also discussed above. Preferably, the movable lever 138 is rotated towards the fixed cylindrical body 136 to move the first and second elongated jaws 104, 106 into the closed position. The movable lever 138 can further have a locking means, such as a ratchet mechanism known in the art, to lock the first and second elongated jaws 104, 106 in the closed position to thereby clamp tissue therebetween. However, because of the configuration of the handle 134, the user can merely keep his/her hand gripped around the fixed cylindrical body 136 and lever 138 to lock the first and second elongated jaws 304, 306 in the closed position without the aid of a locking mechanism.

Once the first and second elongated jaws 304, 306 are clamped onto tissue, the tissue is ablated by an ablation means that supplies ablation energy to at least one of the first and second elongated jaws 304, 306. The ablation energy can take any form known in the art to ablate tissue, the degree of ablation energy is set or predetermined according to the particular type of tissue and/or the particular surgical procedure. In one implementation, at least a portion of one of the first and second ablation surfaces 308, 310 corresponding to one of the first and second elongated jaws 304, 306 has an exposed conductive surface 340, such as a metallic surface. In which case the ablation means comprises means for supplying radio frequency energy to the exposed conductive surface 340. In such a configuration, the instrument 300 is commonly referred to as a monopolar instrument and is used in combination with a grounding plate as is known in the art. Preferably, both of the first and second ablation surfaces 308, 310 corresponding to the first and second elongated jaws 304, 306 have an exposed conductive surface 340. In such a configuration, the instrument 300 is commonly referred to as a bipolar instrument. In either the monopolar or bipolar configuration, surfaces of the instrument other than the exposed conductive surface 310 are coated with an electrical insulation or fabricated from a non-conductive material to prevent electrical energy from injuring unintended tissue. Radio frequency sources for supplying radio frequency energy to electrosurgical instruments are well known in the art. Typically, the radio frequency source is connected to an electrode post 142 by way of a power cord. The electrode post 342 is electrically connected to one or both elongated jaws 304, 306, preferably via the elongated rods 316, 320.

Alternatively, the ablation means comprises means for supplying ultrasonic energy to at least one of the first and second ablation surfaces 308, 310. In which case, ultrasonic energy is delivered to the ablation surfaces 308, 310 of the first and second jaws 304, 306 and may be focused to the tissue surface being ablated, as described elsewhere in this application. An ultrasonic generator, as is known in the art, is used to generate the ultrasonic energy and is delivered to the ablation surfaces 308, 310 of the first and second jaws 304, 306 via the elongated rods 316, 320. The ultrasonic generator can be integral with the instrument 300 or separate therefrom.

Figure 9:
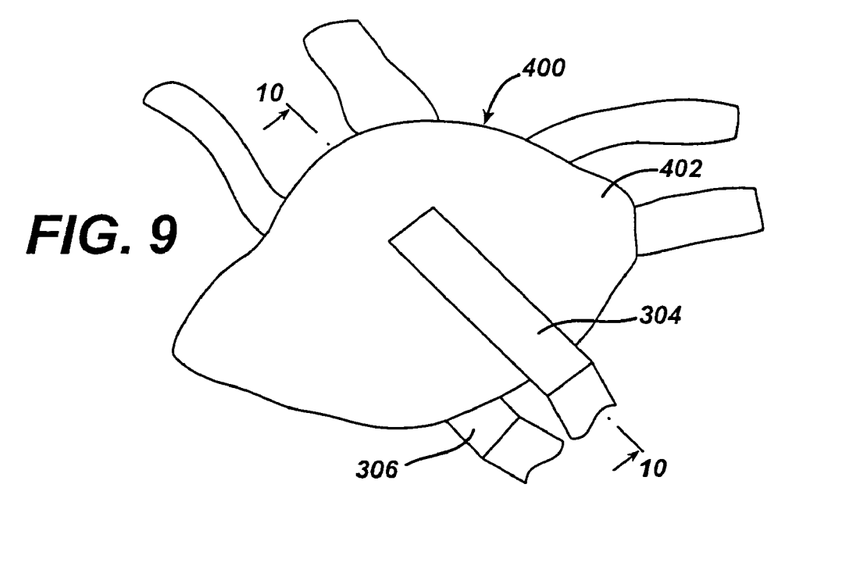
FIG. 9 illustrates an isometric view of the first and second elongated jaws of the surgical instrument of FIG. 1 grasping the left atrium of a heart.
Figure 10:
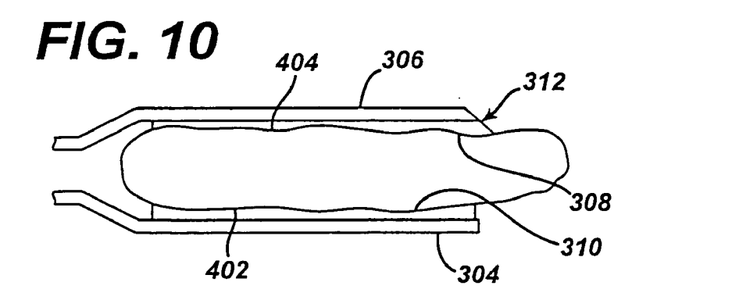
FIG. 10 illustrates a sectional view of FIG. 9 as taken along line 10—10 of FIG. 9.

An exemplary procedure for use with the ablative clamps of the present invention will now be described with regard to FIGS. 9 and 10, and the embodiment of FIGS. 6–8. It will be appreciated by those skilled in the art that the methods described are also applicable to the other embodiments or to other devices. The instruments of the present invention are particularly well suited for performing ablation on open or closed atria. In such a procedure, thermal lesions are created on at least a portion of a heart 400, particularly, the left atrium. After accessing the heart, either by opening the chest or minimally invasively, the first and second elongated jaws 304, 306 are actuated into the open position and placed over the heart such that one of the ablation surfaces corresponds to the anterior cardiac surface 402 of the heart 400 and the other of the ablation surfaces 310 corresponds to the dorsal cardiac surface 404 of the heart 400. The first and second elongated jaws 304, 306 are then clamped in the closed position to compress the heart tissue as shown in FIG. 10. Clamping of the tissue is preferred because it enables good contact between the irregular cardiac tissue and the ablation surfaces 308, 310 of the first and second elongated jaws 304, 306 to create lesions that are continuous and adequately deep. Clamping also helps to remove the blood from the ablated portion thereby minimizing potential thrombus formation.

After the first and second elongated jaws 304, 306 are clamped onto the heart tissue, the ablation energy is applied to one and/or both of the ablation surfaces 308, 310 of the first and second elongated jaws 304, 306. In one configuration, the ablation energy is applied to only the anterior surface if only the anterior ablation is clinically needed. In another configuration, the ablation energy is applied to only the dorsal surface if only the dorsal ablation is clinically needed. In yet another configuration, the ablation energy is applied to both the anterior and dorsal surfaces if there is a need to guarantee transmurality of the lesion. More lesions are created in the same manner, if necessary, and the instrument removed.

Figure 11:
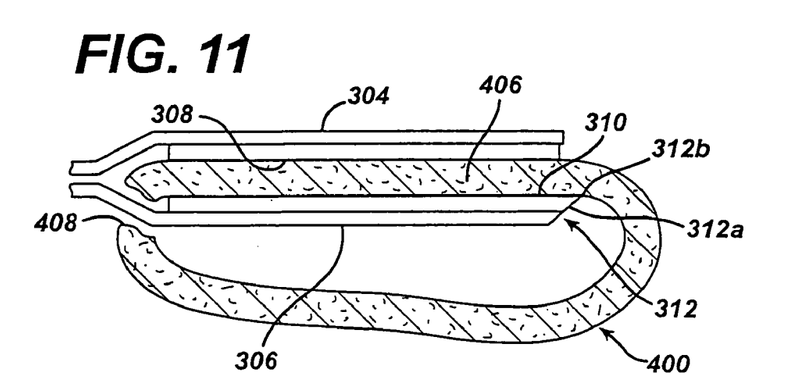
FIG. 11 illustrates a sectional view of the distal end of the surgical instrument of FIG. 6 with the second elongated jaw pierced through a wall of a hollow vessel and a portion of the wall of the hollow vessel clamped between the first and second elongated jaws.

Referring now to FIG. 11, another procedure for use with the instrument 300 of the present invention will be described. The procedure illustrated in FIG. 11 is useful in creating lesions on both sides of a wall 406 of a hollow organ or vessel, such as the heart 400. After accessing the hollow organ or vessel 400 by surgical means known in the art, the wall 406 is pierced with the sharpened leading edge 312b of the pointed distal tip 312 of one of the elongated jaws 306 to create a puncture 408. The elongated jaw 306 is then extended into the puncture 408 and the first and second elongated jaws 304, 306 are actuated into the closed position to clamp the wall 406 therebetween. The ablation energy is then applied to at least one of the first and second instrument jaws 304, 306 to ablate the tissue surfaces of the wall 406. As discussed above, the instrument 300 may be configured such that ablation energy may be applied to either or both of the ablation surfaces 308, 310 of the first and second elongated jaws 304, 306. More lesions are created in the same manner, if necessary, and the instrument removed. The puncture 408 is then closed, if necessary, by standard surgical methods, such as suturing, stapling, or gluing.

Those skilled in the art will appreciate that the instruments of the present invention can be useful in surgical techniques and procedures to perform ablation on closed or open atria. These techniques and procedures could be performed on a stopped heart, or a beating heart, and either through an open incision or a minimally invasive technique. These techniques and procedures could also be performed as a standalone procedure, or after a coronary artery bypass graft (CABG) operation to prophylactically prevent peri/post operative onset of atrial fibrillation (a major morbidity of stopped heart CABG), or at the same time as a valve repair or replacement procedure.

In such techniques and procedures, it is imperative to avoid causing clots to form in the atrium as they can cause stroke. Additionally, in order to have an effective therapy it is necessary to produce a lesion entirely through the myocardium wall. The methods and instruments of the present invention preferably use radio frequency or ultrasound energy delivered to the wall of the atrium to ablate the tissue and cause scars/lesions that form a conduction block and prevent the fibrillation.

Figure 12:
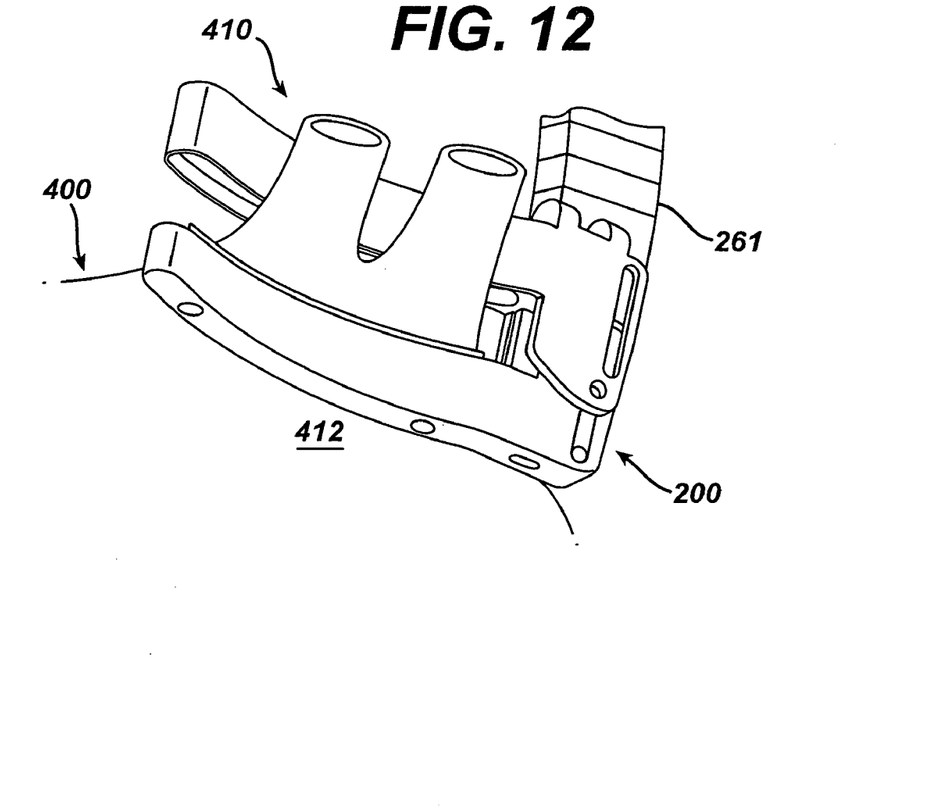
FIG. 12 illustrates the embodiment shown in FIGS. 3–5 clamping the left atrium of the heart surrounding the pulmonary veins.

Referring now to FIG. 12, another procedure for using the ablative clamp according to the present invention is depicted. The surgeon can use the instrument 200, or another instrument described above, or substitute those known in the art, to encircle only the pulmonary veins 410 in the left atrium 412. Alternately, or additionally, the instrument 200, as depicted or described herein, or a combination of instruments described herein, can be used to produce a more complicated ablative pattern in both atria. For example, a lesion(s) that encircle(s) the pulmonary veins connecting both atria to the annulus of the mitral valve may be formed.

While there has been shown and described what is considered to be preferred embodiments of the invention, it will, of course, be understood that various modifications and changes in form or detail could readily be made without departing from the spirit of the invention. The embodiments described are offered as illustrative, and not limiting, on the scope of the invention. It is therefore intended that the invention be not limited to the exact forms described and illustrated, but should be constructed to cover all modifications that may fall within the scope of the appended claims.

The invention claimed is:

1. An apparatus for ablating tissue, the apparatus comprising:
   first and second opposing jaws operative to secure tissue to be ablated therebetween;
   the first jaw having a first ablation surface for directing ablative energy into the tissue;
   the second jaw having a second ablation surface for reflecting ablative energy into the tissue; and
   at least one of the first jaw or the second jaw having a cavity with a transducer element therein and an air backing chamber.

2. The apparatus according to claim 1, further comprising a passage for communication of a cooling fluid to at least one of the first and second elongated jaws.

3. The apparatus according to claim 1, further comprising a heat exchanger for the conduction of heat away from a distal end of the apparatus.

4. The apparatus according to claim 1, wherein the first jaw comprises an ultrasonic transducer for supplying ultrasonic ablative energy to the first ablation surface.

5. The apparatus according to claim 1, wherein the ablative energy directed into the tissue by the first ablative surface is focused at its source.

6. The apparatus according to claim 1, wherein the second ablation surface is shaped to focus the reflected ablative energy.

7. The apparatus according to claim 1, further comprising a temperature probe adjacent one of the first and second ablation surfaces.

8. The apparatus according to claim 1, wherein the ablative energy is one of ultrasonic, microwave, laser radio-frequency and cryoablative energy.

9. The apparatus of claim 1, wherein one of the first and second jaws has a pointed distal tip for piercing tissue.

10. The apparatus of claim 9, wherein the pointed distal tip comprises a tapered surface terminating in a sharp leading edge.

11. The apparatus of claim 1, wherein the first and second jaws maintain at least a substantially parallel relationship between the open and closed positions.

12. The apparatus of claim 11, further comprising:
   biasing means for biasing the first and second jaws in the open position;
   a first elongated rod disposed at a proximal end of the first jaw;
   a second elongated rod disposed at a proximal end of the second jaw;
   an elongated tube having a lumen for disposing the first and second elongated rods;
   wherein at least one of the first and second elongated rods and the elongated tube is operatively connected to the articulation means such that actuation thereof forces the first and second jaws into the closed position against a biasing force of the biasing means.

13. The apparatus of claim 12, wherein the articulation means comprises a handle, the elongated tube and first and second elongated rods having a proximal end operatively connected to the handle, the handle having a fixed portion and a movable lever portion, wherein rotation of the movable lever portion relative to the fixed portion actuates the first and second jaws into the closed position and an opposite rotation of the movable lever portion relative to the fixed portion actuates the first and second jaws into the open position.

14. The apparatus according to claim 1, wherein the first and second jaws are operative to compress tissue therebetween.

* * * * *